US00PP24568P3

(12) United States Plant Patent
Caster et al.

(10) Patent No.: US PP24,568 P3
(45) Date of Patent: Jun. 24, 2014

(54) BLUEBERRY PLANT NAMED 'DRISBLUEEIGHT'

(50) Latin Name: ***Vaccinium corymbosum* L.**
Varietal Denomination: DrisBlueEight

(75) Inventors: Brian K. Caster, Salinas, CA (US); Jennifer K. Izzo, Watsonville, CA (US); Arlen Draper, Payson, AZ (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 70 days.

(21) Appl. No.: 13/507,989

(22) Filed: Aug. 10, 2012

(65) Prior Publication Data

US 2014/0047590 P1 Feb. 13, 2014

(51) Int. Cl.
*A01H 5/00* (2006.01)

(52) U.S. Cl.
USPC ..... Plt./157

(58) Field of Classification Search
USPC ..... Plt./157
See application file for complete search history.

*Primary Examiner* — Kent L Bell

(74) *Attorney, Agent, or Firm* — Jondle Plant Sciences division of Swanson & Bratschun L.L.C.

(57) ABSTRACT

A new and distinct variety of blueberry plant named 'DrisBlueEight' particularly distinguished by having a very low chilling requirement, small plant size with medium productivity and firm, tart berries with dark blue color, is disclosed.

2 Drawing Sheets

Genus and species: *Vaccinium corymbosum* L.
Variety denomination: 'DrisBlueEight'.

BACKGROUND OF THE NEW PLANT

The invention relates to a new and distinct blueberry variety designated 'DrisBlueEight' and botanically known as *Vaccinium corymbosum* L. This new blueberry variety was discovered in Santa Cruz, Calif. in June 2000 and originated from a cross between the proprietary female parent blueberry plant 'MS315' (unpatented) and the proprietary male parent blueberry plant 'MS122' (unpatented). The original seedling of the new variety was first asexually propagated at a nursery in Monterey, Calif. via softwood cuttings. 'DrisBlueEight' was subsequently asexually propagated and underwent further testing at a nursery in Santa Cruz, Calif. for thirteen years. The present invention has been found to be stable and reproduce true to type through successive asexual propagations via softwood cuttings.

Plant Breeder's Rights for this variety have not been applied for. 'DrisBlueEight' has not been made publicly available or sold more than one year prior to the filing date of this application.

SUMMARY OF THE INVENTION

The following are the most outstanding and distinguishing characteristics of this new cultivar when grown under normal horticultural practices in Santa Cruz, Calif.

1. A very low chilling requirement;
2. Small plant size with medium productivity; and
3. Firm, tart berries with dark blue color.

DESCRIPTION OF THE PHOTOGRAPHS

This new blueberry plant is illustrated by the accompanying photographs which show fruit of the plant as well as the flowers and leaves. The colors shown are as true as can be reasonably obtained by conventional photographic procedures. The photographs are of plants that are 12 years old.

DESCRIPTION OF THE NEW CULTIVAR

Figure 1:
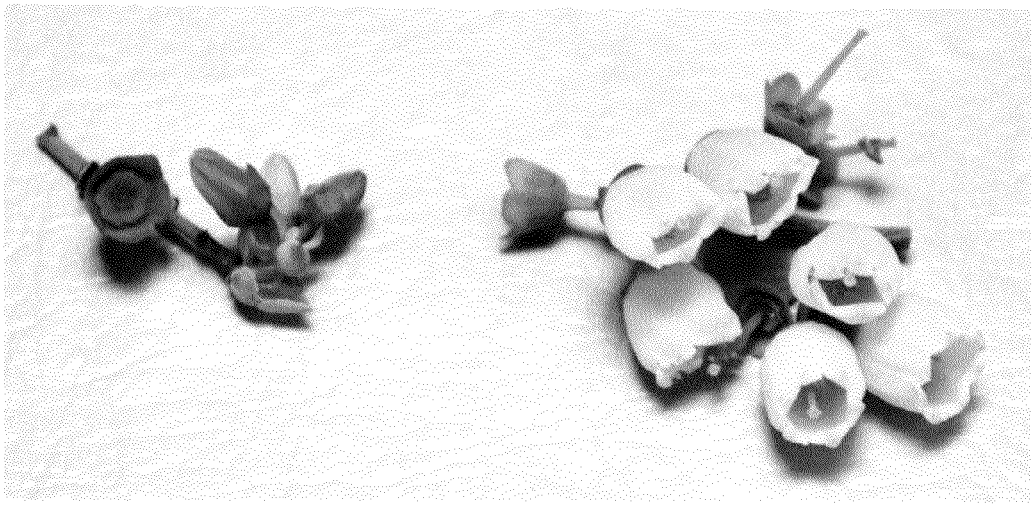
FIG. 1 shows a close-up of the mature flowers.
Figure 2:
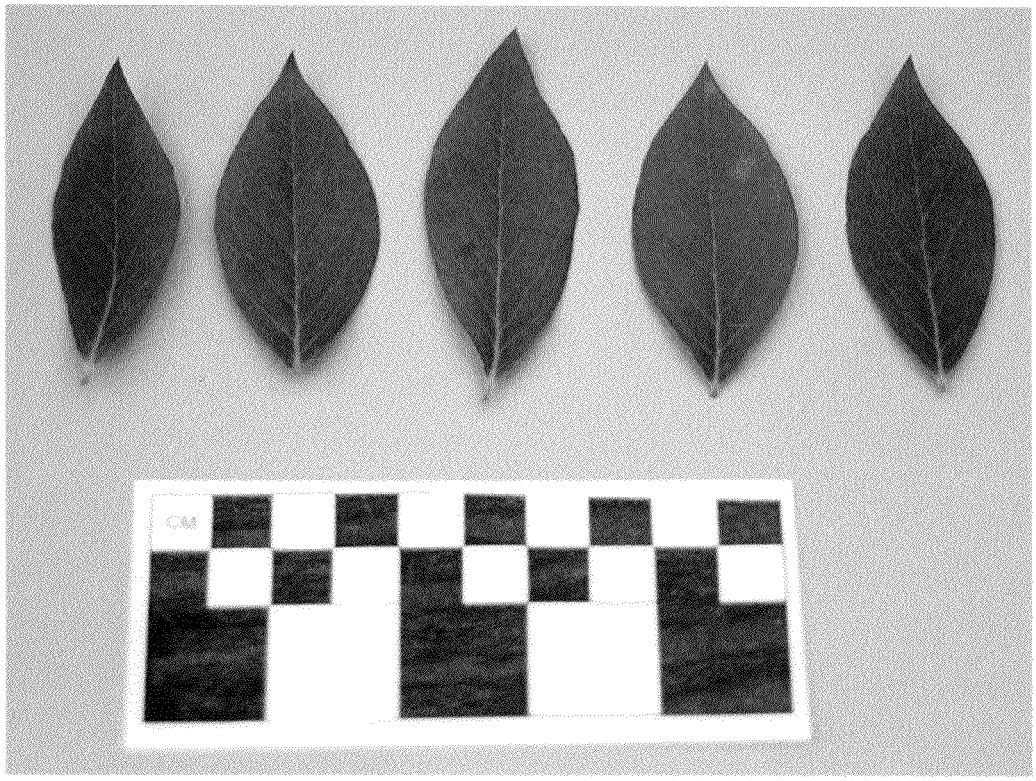
FIG. 2 shows a close-up of the leaves.
Figure 3:
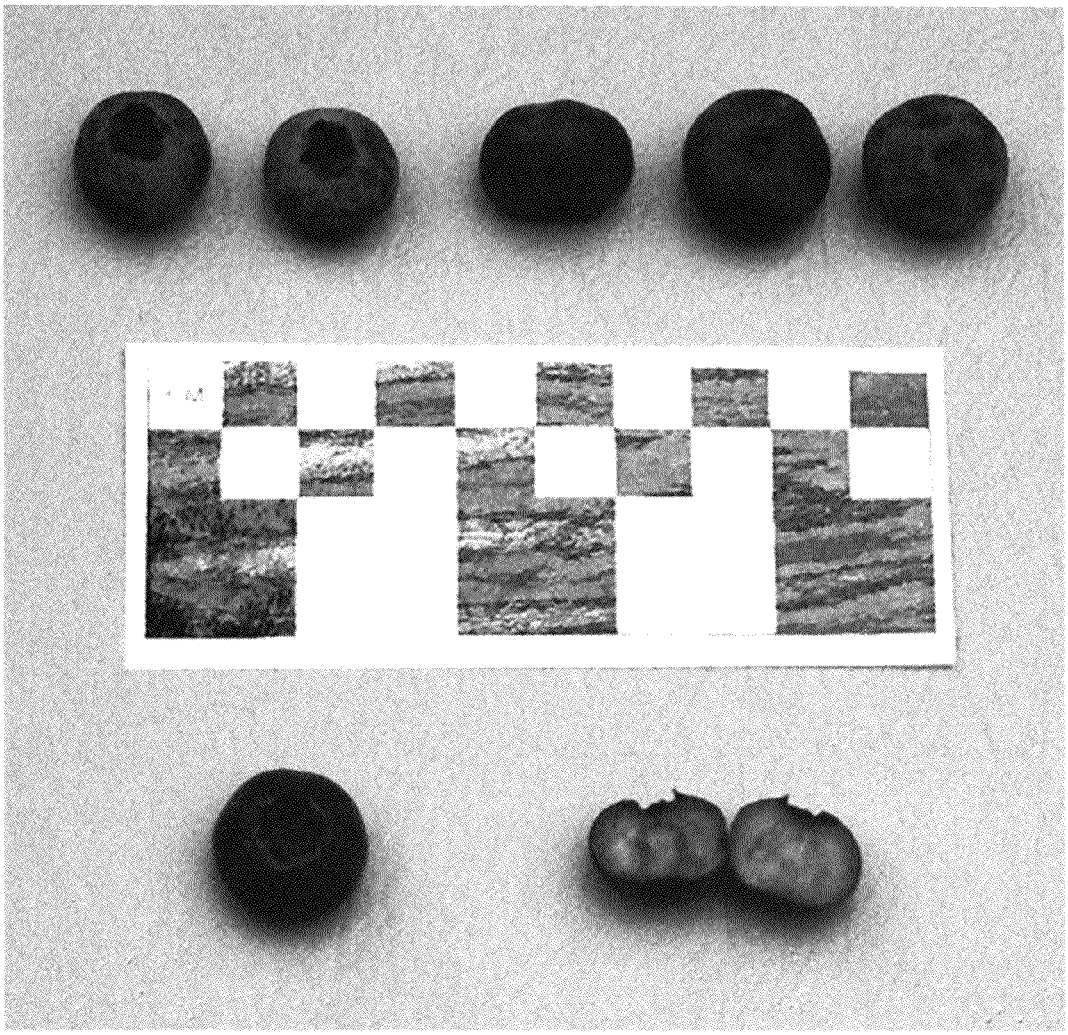
FIG. 3 shows a close-up of the whole fruit and a cross-section of the fruit.

The following detailed description sets forth the distinctive characteristics of 'DrisBlueEight'. The data which define these characteristics is based on observations taken in Santa Cruz, Calif. from 2000-2012. This description is in accordance with UPOV terminology. Color designations, color descriptions, and other phenotypical descriptions may deviate from the stated values and descriptions depending upon variation in environmental, seasonal, climatic and cultural conditions. 'DrisBlueEight' has not been observed under all possible environmental conditions. The botanical description of 'DrisBlueEight' was taken from 12 year-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION

Classification:

*Family.*—Ericaceae.
*Botanical.*—*Vaccinium corymbosum* L.
*Common name.*—Blueberry.
*Variety name.*—'DrisBlueEight'.

Parentage:

*Female parent.*—The proprietary blueberry plant 'MS315' (unpatented).

*Male parent*.—The proprietary blueberry plant 'MS122' (unpatented).

Plant:

*Size*.—Small.
*Height*.—81.1 cm.
*Width*.—93.2 cm.
*Length/width ratio*.—0.9.
*Plant vigor*.—Weak to medium.
*Growth habit*.—Semi-erect to upright.
*Cold hardiness*.—USDA hardiness zone 8B or higher.
*Chilling requirement*.—Very low; 150-250 chilling hours.
*Propagation*.—Soft wood cuttings.
*Time of vegetative bud burst*.—Early.
*Fruiting type*.—Only on one-year-old shoots.
*Cane renewal*.—Weak.
*Cane internode length* (*upper half on one-year old shoot*).—24.44 mm.
*One-year old canes* (*young canes*).—Length: 37.85 cm. Diameter at the base: 7.70 mm. Diameter at the tip: 3.95 mm. Texture: Smooth. Color (One-year old shoot, branch and canes): RHS N144A (Medium yellow-green).
*Five-year old canes* (*mature canes*).—Length: 67.18 cm. Diameter at the base: 13.07 mm. Diameter at the tip: 5.94 mm. Texture: Rough. Color: RHS 146C (Medium yellow-green).

Leaves:

*Length*.—Medium; 6.01 cm.
*Width*.—Medium; 3.06 cm.
*Length/width ratio*.—2.0; longer than broad.
*Shape*.—Elliptic.
*Apex*.—Acute to cuspidate.
*Base*.—Obtuse.
*Margin*.—Entire.
*Glossiness*.—Medium.
*Pubescence*.—Glabrous (Absent).
*Sheath*.—Absent.
*Arrangement*.—Alternate.
*Venation*.—Reticulate.
*Color*.—Upper surface: Dark; RHS 137A (Dark green). Lower surface: Light; RHS N138C (Light green).
*Appearance of leaf bud*.—Medium.
*Leaf internode length* (*one-year old shoot, upper half*).—Medium; 7.84 mm.

Petiole:

*Length*.—3.4 mm.
*Diameter*.—1.46 mm.
*Color*.—RHS 144D (Light yellow-green).

Flowers:

*Length* (*excluding peduncle*).—Medium; 10.63 mm.
*Diameter*.—6.73 mm.
*Length/width ratio*.—1.6.
*Petal color*.—RHS 157C (Light green-white).
*Flower arrangement*.—Thyrse.
*Flower bud*.—Length: 9.0 mm. Width: 3.0 mm. Color on mature buds: RHS 65C (Medium red-purple) and RHS 155B (White).
*Petal number*.—5 fused petals.
*Petal shape*.—Orbicular.
*Petal apex*.—Lobed.
*Petal margin*.—Fused.
*Petal length*.—10.63 mm.
*Petal width*.—4.64 mm.
*Fragrance*.—Very faint or absent.
*Time of beginning flowering on one-year shoot*.—Medium.
*Time of flowering* (50% *full bloom*).—Early; March 15.
*Pedicel*.—Length: 7.15 mm. Diameter: 0.89 mm. Color: RHS 144C (Medium yellow-green).
*Corolla*.—Aperture diameter: 4.35 mm. Shape: Urceolate. Size of corolla tube: Medium. Corolla tube length: 10.63 mm. Corolla tube diameter: 6.73 mm. Corolla tube color: Medium; RHS 65C (Medium red-purple). Ridges on tube: Present.
*Peduncle length*.—21.31 mm.

Reproductive organs:

*Style length* (*including stigma*).—Medium; 9.09 mm.
*Style color*.—RHS 144C (Medium yellow-green).
*Ovary color*.—RHS 136D (Light green).
*Pollen amount*.—High.
*Pollen color*.—RHS 9D (Light yellow).
*Anther color*.—RHS 168C (Medium greyed-orange).

Fruit:

*Size*.—Medium to large.
*Length*.—10.61 mm.
*Width*.—15.38 mm.
*Length/width ratio*.—0.7.
*Fruit pedicel diameter*.—3.69 mm.
*Weight*.—2.2 g.
*Number of berries per cluster*.—5.
*Cluster density*.—Sparse or low.
*Shape in longitudinal sections*.—Oblate.
*Intensity of green color* (*immature fruit with bloom*).—Light or clear to medium; RHS 144D (Light yellow-green).
*Color of skin* (*immature fruit without bloom*).—RHS N92 (Dark violet-blue).
*Color of skin* (*mature fruit without bloom*).—RHS N186A (Dark blue).
*Color of skin* (*mature fruit with bloom*).—RHS 107C (Light blue).
*Intensity of bloom* (*mature fruit*).—Medium.
*Sepals*.—Attitude of sepals: Incurving. Sepal number: 5 fused. Apex: Rounded lobed. Margin: Fused.
*Calyx*.—Diameter of basin: Medium; 7.44 mm. Depth of basin: Medium; 1.89 mm. Diameter/depth ratio: 3.9.
*Flesh color*.—RHS 193B (Light green).
*Firmness*.—Firm.
*Sweetness*.—High.
*Acidity*.—Low.
*Time of beginning of fruit ripening* (*one-year old shoots*).—Medium.
*Harvest season*.—Early to medium.
*Harvest interval*.—June 5-July 19.

Seeds:

*Length*.—1.62 mm.
*Width*.—0.92 mm.
*Length/width ratio*.—1.8.
*Abundance*.—Low.
*Color*.—RHS 165B (Medium greyed-orange).

Resistance to pests and diseases: Data not available.

COMPARISON WITH PARENTAL AND COMMERCIAL VARIETIES

'DrisBlueEight' differs from parental variety 'MS315' (unpatented) in that 'DrisBlueEight' has a very low chilling requirement, whereas 'MS315' has a medium chilling requirement.

'DrisBlueEight' differs from parental variety 'MS122' (unpatented) in that 'DrisBlueEight' has a very low chilling requirement, whereas 'MS 122' has a medium chilling requirement.

'DrisBlueEight' differs from the commercial variety 'DrisBlueOne' (U.S. Plant Pat. No. 20,449) in that 'DrisBlueEight' has berries with high sweetness, an early time of vegetative bud burst, and leaves with an acute to cuspidate apex and an obtuse base, whereas 'DrisBlueOne' has berries with medium sweetness, a medium time of vegetative bud burst, and leaves with a broadly acute apex and broadly acute to rounded base. Additionally, 'DrisBlueEight' has a very low chilling requirement, whereas 'DrisBlueOne' has a medium chilling requirement.

'DrisBlueEight' differs from the commercial variety 'DrisBlueTwo' (U.S. Plant Pat. No. 20,488), in that 'DrisBlueEight' has leaves with an entire margin, oblate shaped berries, and a high amount of pollen, whereas 'DrisBlueTwo' has leaves with serrulate margin, nearly spherical shaped berries and a sparse amount of pollen. Additionally, 'DrisBlueEight' has a very low chilling requirement, whereas 'DrisBlueTwo' has a medium chilling requirement.

We claim:

1. A new and distinct variety of blueberry plant named 'DrisBlueEight' as shown and described herein.

* * * * *